United States Patent [19]

Curran

[11] 4,092,418

[45] May 30, 1978

[54] CERTAIN 1-CARBOTHIOAMIDES OF 1,5-NAPHTHYRIDINE DERIVATIVES

[75] Inventor: Adrian Charles Ward Curran, South Cave, England

[73] Assignee: John Wyeth & Brother Limited, Maidenhead, England

[21] Appl. No.: 785,637

[22] Filed: Apr. 7, 1977

Related U.S. Application Data

[63] Continuation-in-part of Ser. No. 671,521, Mar. 29, 1976, abandoned, which is a continuation-in-part of Ser. No. 553,964, Feb. 28, 1975, Pat. No. 3,960,876.

[30] Foreign Application Priority Data

Mar. 5, 1974    United Kingdom .................. 9764/74
Jul. 12, 1974    United Kingdom ............... 30935/74

[51] Int. Cl.$^2$ .................. A61K 31/435; C07D 471/04
[52] U.S. Cl. .............................. 424/256; 260/294.8 C
[58] Field of Search .................. 260/294.8 C; 424/256

[56] References Cited

U.S. PATENT DOCUMENTS

| | | | |
|---|---|---|---|
| 3,149,104 | 9/1964 | Lesher et al. | 260/295 N |
| 3,745,162 | 7/1973 | Heisley | 260/283 D |

*Primary Examiner*—Alan L. Rotman
*Attorney, Agent, or Firm*—Arthur E. Wilfond

[57] ABSTRACT

The invention relates to thioureas which are derivatives of 1,5-Naphthyridines. The compounds are anti-ulcer agents or intermediates therefor.

8 Claims, No Drawings

CERTAIN 1-CARBOTHIOAMIDES OF 1,5-NAPHTHYRIDINE DERIVATIVES

This application is a continuation-in-part of my application U.S. Ser. No. 671,521, filed Mar. 29, 1976, now abandoned, which in turn is a continuation-in-part of my application U.S. Ser. No. 553,964 filed Feb. 28, 1975 now U.S. Pat. No. 3,960,876.

This invention relates to novel organic nitrogen compounds, to processes for preparing them and to pharmaceutical compositions containing them.

According to the invention there is provided compounds of formula (I)

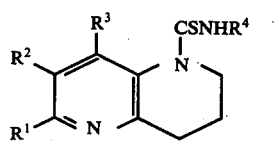

and pharmaceutically acceptable acid addition salts thereof wherein $R^1$, $R^2$ and $R^3$ are the same or different and represent a hydrogen atom or lower alkyl of 1-6 carbon atoms which may be substituted by lower alkoxy of 1-6 carbon atoms and $R^4$ is hydrogen or alkyl of 1-3 carbon atoms.

When any $R^1$, $R^2$ or $R^3$ is a lower alkyl radical then this may be a straight or branched chain, having from 1 to 6 carbon atoms, e.g. methyl, ethyl, n-, and iso-propyl and n, s- and t- butyl. The term alkyl radical is also intended to embrace cyclic alkyl radicals e.g. cyclobutyl, cyclopentyl and cyclohexyl.

The term "lower alkoxy" as used in this specification means alkoxy radicals having from 1 to 6 carbon atoms e.g. methoxy, ethoxy, propoxy, butoxy, pentoxy and hexoxy.

Preferably when $R^1$ and $R^2$ or $R^2$ and $R^3$ are both alkyl, they are selected from normal and secondary alkyl groups. More preferred compounds are those in which $R^1$, $R^2$ and $R^3$ are selected from hydrogen and methyl. Particulary preferred compounds are those in which at least one of $R^1$, and $R^2$ and $R^3$ is methyl and the others are hydrogen.

The group $R^4$ may be methyl, ethyl or n-propyl. Preferably $R^4$ is methyl.

Compounds of formula I wherein $R^4$ is hydrogen or alkyl of 1-3 carbon atoms are anti-ulcer agents, which are active in one or more of the following pharmacological tests namely anti-ulcer, anti-secretory or gastric anti-histamine activity. Activity in any one of these tests denotes an anti-ulcer agent.

The invention includes processes for preparing the compounds of formula I.

A process for preparing compounds of formula I wherein $R^4$ is alkyl of 1-3 carbon atoms comprises reacting a compound of formula II

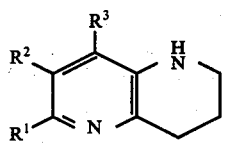

wherein $R^1$, $R^2$ and $R^3$ are as defined in connection with formula I with an isothiocyanate of formula $R^4NCS$ wherein $R^4$ is defined immediately above.

Compounds of formula I, wherein $R^4$ is hydrogen may be prepared by hydrolysing a compound of formula I wherein $R^4$ is lower alkanoyl or aroyl. These starting compounds may be prepared by treating a compound of formula II as defined above with an isothiocyanate $R^4NCS$ where $R^4$ is lower alkanoyl or aroyl.

Examples of aroyl groups are benzoyl and substituted benzoyl e.g. halobenzoyl, such as chlorobenzoyl. The lower alkanoyl group is one having from 2 to 7 carbon atoms e.g. acetyl, propionyl, butyryl, pentanoyl and hexanoyl.

The hydrolysis may be carried out by treatment with a suitable base e.g. an alkali or alkaline earth metal hydroxide. Conveniently sodium or potassium hydroxide may be used. Alternatively acid hydrolysis may be used.

The compounds of formula I can form acid addition salts with inorganic acids e.g. hydrochloric, hydrobromic, sulphuric or nitric acids, or organic acids e.g. citric, fumaric, maleic or tartaric acids. These acid addition salts are included in the invention.

The starting compounds of formula II are known compounds or may be prepared by methods known for analogous compounds. Methods for the preparation of compounds of formula II are described in the literature. A convenient method is reduction of the corresponding 1,5-naphthyridines as described in Advances in Heterocyclic Chemistry, 11, 1970 at pages 158-161. The 1,5-naphthyridines may be prepared as described in the same article at pages 136-140.

Thus 3-amino pyridine III may be condensed with a glycerol of formula IV to give the

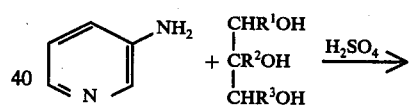

III        IV

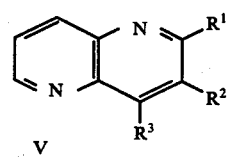

V

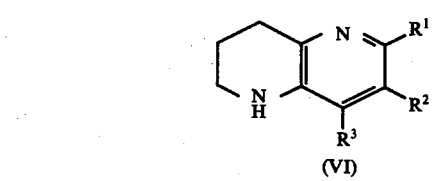

(VI)

1,5-naphthyridine of formula V which is reduced e.g. by hydrogenation over platinum oxide, to the 1,2,3,4-tetrahydro-1,5-naphthyridine of formula (VI). In formula IV, V and VI, $R^1$, $R^2$ and $R^3$ are as defined in connection with formula I.

If $R^1$ and $R^3$ are different in formula (IV) then a mixture of products of formula V (in which $R^1$ or $R^3$ is adjacent to the nitrogen atom) may be formed which can be separated by standard methods e.g. gas liquid chromatography.

Alternatively a substituted pyridine of formula IIIa

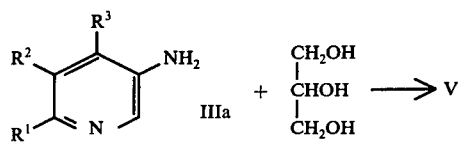

may be reacted with glycerol to give compound V which is then reduced to compound (VI). This route is useful when $R^1$ and $R^3$ are different.

As stated above the active compounds of formula I, wherein $R^4$ is hydrogen, or alkyl of 1–3 carbon atoms, are anti-ulcer agents which display activity in tests for one or more of the following: anti-ulcer, anti-secretory or gastric anti-histamine activity. Anti-ulcer activity is determined by the method of Brodie and Hanson, J. Applied Physiology, 15, 291, 1960.

Anti-secretory activity and gastric antihistamine activity are determined by the method of H. Shay, D. Sun and H. Greenstein, Gastroenterology 1954, 26, 906-13.

The invention includes a pharmaceutical composition comprising an active compound of formula I (as defined immediately above) including non-toxic salts thereof, and a pharmaceutically acceptable carrier.

For the pharmaceutical carrier any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be capsule, cachet or tablet itself, or it can be the appropriate number of any of these in packaged form.

The quantity of active ingredient in a unit dose of composition may be carried or adjusted from 5 mg. or less to 500 or more, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminum hydroxide, magnesium hydroxide or bismuth carbonate, aluminium glycinate, calcium carbonate magnesium trisilicate, sodium bicarbonate or the alumina gel described in British Specification No. 1,284,394.

The invention is illustrated by the following Examples. Temperatures are in ° C.

EXAMPLE 1

1,2,3,4-Tetrahydro-1-(N-methylthiocarboxamido)-1,5-naphthyridine 1,5-Naphthyridine was prepared from 3-aminopyridine according to the method described in J. Org. Chem., 1963, 1757 and was isolated as colourless needles from n-hexane m.p. 69° C (lit. 74°). 1,5-Naphthyridine (2.6 g.) was hydrogenated in 95% ethanol over $PtO_2$ catalyst under atmospheric conditions to give 1,2,3,4-tetrahydro-1,5-naphthyridine as colourless needles (2.51 g.).

1,2,3,4-Tetrahydro-1,5-naphthyridine (1.34 g., 0.01 mol.) was dissolved in acetonitrile (12 ml.) and treated with methylisothiocyanate (0.73 g., 0.01 mol.) and the mixture heated at reflux with stirring for 3 hours. The solvent was removed in vacuo and the residue recrystallised from isopropanol to give the title compound as colourless needles (0.9 g.) m.p. 120° C. (Found: C, 58.4; H, 6.6; N, 20.3. $C_{10}H_{13}N_3S$ requires: C, 57.9; H, 6.3; N, 20.3%).

EXAMPLE 2

1-(N-Ethylthiocarboxamido)-1,2,3,4-tetrahydro-1,5-naphthyridine 1,2,3,4-Tetrahydro-1,5-naphthyridine is treated with ethyl isothiocyanate according to the procedure of Example 1 to obtain the title compound.

EXAMPLE 3

1,2,3,4-Tetrahydro-1,5-naphthyridine-1-thiocarboxamide 1,2,3,4-Tetrahydro-1,5-naphthyridine is treated with p-chlorobenzoyl isothiocyanate according to the method of Example 1 to give 1-(N-p-Chlorobenzoylthiocarboxamido)-1,2,3,4-tetrahydro-1,5-naphthyridine which is hydrolysed with 10% sodium hydroxide to give 1,2,3,4-tetrahydro-1,5-naphthyridine-1-thiocarboxamide.

EXAMPLE 4

1-(N-methylthiocarboxamido)-6-methyl-1,2,3,4-tetrahydro-1,5-naphthyridine

2-Methyl-5,6,7,8-tetrahydronaphthyridine is treated with methyl isothiocyanate in the manner described in Example 1 for the unsubstituted compound to obtain the title compound (in the product the 5-nitrogen atom of the starting material is renumbered 1 and the 2-methyl substituent of the starting material is numbered 6).

EXAMPLE 5

1-(N-ethylthiocarboxamido)-8-methyl-1,2,3,4-tetrahydro-1,5-naphthyridine

4-Methyl-5,6,7,8-tetrahydro-1,5-naphthyridine is treated with ethyl isothiocyanate according to the procedure of Example 1 to obtain the title compound. (In the product the 5-nitrogen atom of the starting compound is renumbered 1 and the 4-methyl substituent is renumbered 8).

EXAMPLE 6

1-(N-methylthiocarboxamido)-6,8-Dimethyl-1,2,3,4-tetrahydro-1,5-naphthyridine 2,4-Dimethyl-5,6,7,8-tetrahydro-naphthyridine is treated with methyl isothiocyanate according to the procedure of Example 1 to obtain the title compound. (In the product the 5-nitrogen atom of the starting compound is renumbered 1 and the 2,4-methyl substituents are renumbered 6,8.)

EXAMPLE 7

1-(N-benzoyl)thiocarboxamido-1,2,3,4-tetrahydro-1,5-naphthyridine

A solution of 1,2,3,4-tetrahydro-1,5-naphthyridine (2.68g, 0.02 mole) prepared as described above, in acetonitrile (20 ml) use treated dropwise with stirring with a solution of benzoyl isothiocyanate (3.62 g, 0.02 mole) in acetonitrile (5 ml). After ¼ hour the precipitate was removed by filtration and washed with acetonitrile to give 1,2,3,4-tetrahydro-1,5-naphthyridine-1-(N-benzoyl) thiocarboxamide (5.2 g, 88%) m.p. 177°–9° decomp. (Found: C, 64.5; H, 5.2; N, 14.5; $C_{16}H_{15}N_3OS$ requires C, 64.6 H, 5.1; N, 14.1%).

The product may be hydrolysed to give 1,2,3,4-tetrahydro-1,5-naphthyridine-1-thiocarboxamide.

I claim:

1. A compound of formula (I)

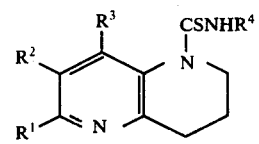

or a pharmaceutically acceptable acid addition salt thereof wherein $R^1$, $R^2$ and $R^3$ are the same or different and represent a hydrogen atom or lower alkyl of 1-6 carbon atoms which may be substituted by lower alkoxy of 1-6 carbon atoms and $R^4$ is hydrogen or alkyl of 1-3 carbon atoms, with the proviso that when $R^1$ and $R^2$ or $R^2$ and $R^3$ are both alkyl they are selected from normal and secondary alkyl groups.

2. A compound of formula I

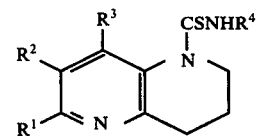

when $R^1$, $R^2$ and $R^3$ are selected from hydrogen and methyl.

3. A compound of claim 2, wherein $R^4$ is methyl.

4. A compound of claim 2 which is 1,2,3,4-tetrahydro-1-(N-methylthiocarboxamido)-1,5,-naphthyridine.

5. A compound of claim 2 which is 1,2,3,4-tetrahydro-1-thiocarboxamido-1,5-naphthyridine.

6. A pharmaceutical composition for use in treating gastric ulcers comprising an effective amount of a compound as claimed in claim 1 and a pharmaceutically acceptable carrier.

7. A pharmaceutical composition as claimed in claim 6 in unit oral dosage form.

8. A pharmaceutical composition as claimed in claim 6 wherein the active ingredient is 1,2,3,4-tetrahydro-1-(N-methylthiocarboxamido)-1,5-naphthyridine.

* * * * *